US012447070B2

(12) United States Patent
Chen et al.

(10) Patent No.: US 12,447,070 B2
(45) Date of Patent: Oct. 21, 2025

(54) REUSABLE ABSORBENT INSERTS AND ASSEMBLIES

(71) Applicant: The Procter & Gamble Company, Cincinnati, OH (US)

(72) Inventors: Yin Chen, Königstein (DE); Udo Friedel Schoenborn, Bad Soden (DE); Deepika Dayal Mathur, Hessen (DE)

(73) Assignee: The Procter & Gamble Company, Cincinnati, OH (US)

( * ) Notice: Subject to any disclaimer, the term of this patent is extended or adjusted under 35 U.S.C. 154(b) by 470 days.

(21) Appl. No.: 17/980,634

(22) Filed: Nov. 4, 2022

(65) Prior Publication Data

US 2023/0146569 A1 May 11, 2023

Related U.S. Application Data

(60) Provisional application No. 63/278,214, filed on Nov. 11, 2021.

(51) Int. Cl.

| | |
|---|---|
| ***A61F 13/15*** | (2006.01) |
| ***A61F 13/49*** | (2006.01) |
| ***A61F 13/505*** | (2006.01) |
| *A61F 13/45* | (2006.01) |

(52) U.S. Cl.

CPC ........ *A61F 13/4906* (2013.01); *A61F 13/505* (2013.01); *A61F 2013/4512* (2013.01)

(58) Field of Classification Search

CPC ................ A61F 13/4906; A61F 13/505; A61F 2013/4512

USPC ........... 604/385.14, 385.15, 385.19, 385.201

See application file for complete search history.

(56) References Cited

U.S. PATENT DOCUMENTS

| | | | | |
|---|---|---|---|---|
| 1,353,196 A | | 9/1920 | Weissman | |
| 5,429,627 A | | 7/1995 | Johnson et al. | |
| 5,707,364 A | * | 1/1998 | Coates | A61F 13/622 604/385.01 |
| 8,409,163 B2 | | 4/2013 | Labit | |
| 8,968,264 B2 | | 3/2015 | Coates | |

(Continued)

FOREIGN PATENT DOCUMENTS

| | | | | |
|---|---|---|---|---|
| GB | 2452052 A | * | 2/2009 | A61F 13/493 |
| GB | 2543024 A | | 4/2017 | |
| WO | 9424973 A1 | | 11/1994 | |

OTHER PUBLICATIONS

Extended European Search Report and Search Opinion; Application No. 22205595.6; dated Mar. 15, 2023; 7 pages.

*Primary Examiner* — Jacqueline F Stephens

(74) *Attorney, Agent, or Firm* — Anna E. Haller; Daniel S. Albrecht

(57) ABSTRACT

Embodiments relate to reusable absorbent inserts, assemblies, and methods for use, the inserts including a configurable pad and pad collection sleeve. The configurable pad includes a first section and a second section, the second section separated from the first section at least partially by a folding guide. The configurable pad has an unfolded pad plan surface area comprising an unfolded pad width when the reusable absorbent insert is in an unfolded, flat-out configuration. The pad collection sleeve has an unfolded sleeve plan surface area including an unfolded sleeve width when the reusable absorbent insert is in an unfolded, flat-out configuration. The unfolded pad width is greater than or substantially equal to the unfolded sleeve width.

18 Claims, 10 Drawing Sheets

(56) References Cited

U.S. PATENT DOCUMENTS

| | | | |
|---|---|---|---|
| 9,138,358 | B2 | 9/2015 | Catoe |
| 10,231,888 | B2 | 3/2019 | Mandell |
| 10,842,684 | B2 | 11/2020 | Mergens |
| 2011/0213327 | A1 | 9/2011 | Oprita et al. |
| 2014/0018756 | A1 | 1/2014 | De Bruin et al. |
| 2014/0296820 | A1 | 10/2014 | Malone |
| 2016/0317361 | A1* | 11/2016 | Mergens ............... A61F 13/472 |
| 2018/0028370 | A1* | 2/2018 | Mandell ................ A61F 13/472 |

* cited by examiner

REUSABLE ABSORBENT INSERTS AND ASSEMBLIES

CROSS REFERENCE TO RELATED APPLICATIONS

This application claims the benefit, under 35 U.S.C. § 119(e), of U.S. Provisional Application No. 63/278,214, filed Nov. 11, 2021, which is incorporated by reference herein in its entirety.

TECHNICAL FIELD

The present specification generally relates to reusable absorbent inserts and absorbent assemblies including the same, and in particular to systems and methods for use of the reusable absorbent inserts and absorbent assemblies.

BACKGROUND

Infants and other incontinent individuals wear absorbent articles and assemblies such as diapers or absorbent pants to receive and contain urine and other body fluids such as a feces. Such absorbent articles may include reusable absorbent inserts. However, while the reusable absorbent inserts may be cleaned for reuse, they may take an extended period of time to dry after such cleaning.

Based on the foregoing, there is a need for alternative absorbent inserts and assemblies and methods of use and manufacture to more efficiently absorb bodily fluids and allow for decreased drying times after cleaning.

SUMMARY

According to the subject matter of the present disclosure, a reusable absorbent insert comprises a configurable pad and pad collection sleeve. The configurable pad includes a first section and a second section, the second section separated from the first section at least partially by a folding guide. The configurable pad has an unfolded pad plan surface area comprising an unfolded pad width when the reusable absorbent insert is in an unfolded, flat-out configuration. The pad collection sleeve has an unfolded sleeve plan surface area including an unfolded sleeve width when the reusable absorbent insert is in an unfolded, flat-out configuration. The unfolded pad width is greater than or substantially equal to the unfolded sleeve width.

In another embodiment, an absorbent assembly comprises an outer shell comprising a first layer of material and a second layer of material, the outer shell defining an interior pocket at least partially between the first layer of material and the second layer of material, and a reusable absorbent insert configured to be received in the interior pocket of the outer shell of the absorbent assembly. The reusable absorbent insert comprises a configurable pad, the configurable pad comprising a first section and a second section, the second section separated from the first section at least partially by a folding guide, and pad collection sleeve. The configurable pad has an unfolded pad plan surface area comprising an unfolded pad width when the reusable absorbent insert is in an unfolded, flat-out configuration, the pad collection sleeve has an unfolded sleeve plan surface area comprising an unfolded sleeve width when the reusable absorbent insert is in an unfolded, flat-out configuration, and the unfolded pad width is greater than or substantially equal to the unfolded sleeve width.

In yet another embodiment, a method of folding a reusable absorbent insert comprises folding a first section of a configurable pad over a second section of the configurable pad along a folding axis of a folding guide to form a semi-folded configuration, the folding guide at least partially separating the second section from the first section, the configurable pad having an unfolded pad plan surface area comprising an unfolded pad width when the reusable absorbent insert is in an unfolded, flat-out configuration, the semi-folded configuration comprising a semi-folded pad width, and the folding axis being transverse to the unfolded pad width and the semi-folded pad width. The method further comprises folding a pad collection sleeve along an axis parallel to the semi-folded pad width into a folded, final configuration that at least partially covers the configurable pad, the pad collection sleeve having an unfolded sleeve plan surface area comprising an unfolded sleeve width when the reusable absorbent insert is in an unfolded, flat-out configuration, the unfolded pad width being greater than or substantially equal to the unfolded sleeve width and substantially equal to the semi-folded pad width.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
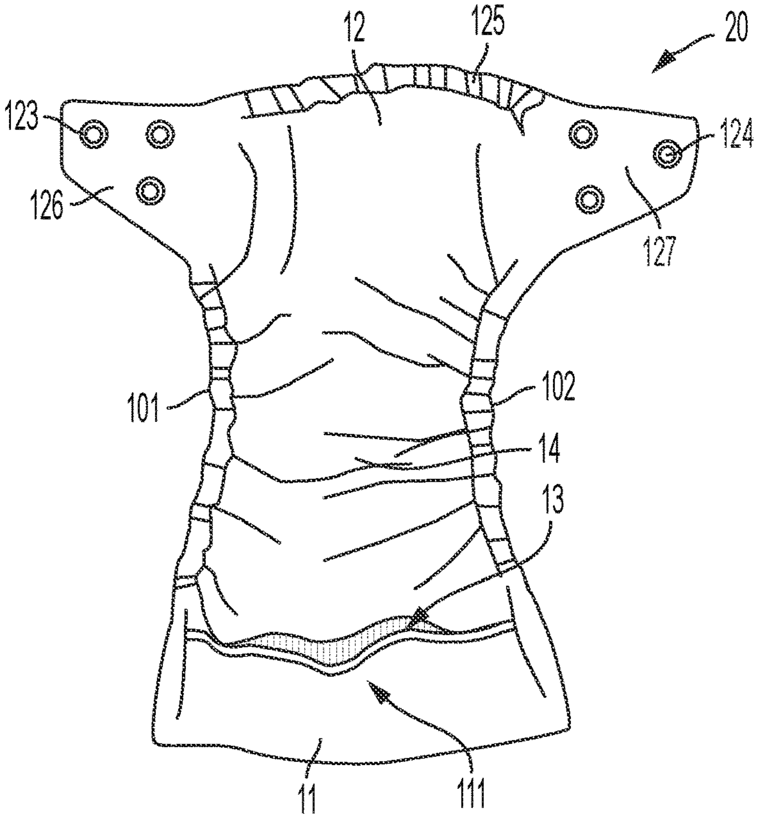
FIG. 1 is an interior side view of an absorbent assembly, showing an interior portion that faces toward a wearer, according to one or more embodiments shown and described herein.

Reference will now be made in detail to embodiments of reusable absorbent inserts and assemblies, examples of which are illustrated in the accompanying drawings. Embodiments herein are directed to alternative absorbent inserts and assemblies and methods of use and manufacture to more efficiently absorb bodily fluids and allow for decreased drying times after cleaning. Whenever possible, the same reference numerals will be used throughout the drawings to refer to the same or like parts. Various embodiments of such absorbent patents, systems, and methods will be described in further detail herein with specific reference to the appended drawings. Those of ordinary skill in the art will understand that the absorbent inserts and assemblies and methods of use and manufacture described herein and illustrated in the accompanying drawings are non-limiting example forms and that the scope of the various non-limiting forms of the present disclosure. The features illustrated or described in connection with one non-limiting form may be combined with the features of other non-limiting forms. Such modifications and variations are intended to be included within the scope of the present disclosure.

The reusable absorbent inserts described herein are configured to be manufactured to be in a long, thin form in an initial unfolded, flat-out configuration such that a user may fold them as described in embodiments herein into a customizable shape having a customizable size and or thickness prior to use with a reusable absorbent assembly such as a reusable diaper. After use, the reusable absorbent inserts may be unfolded to arrive back at the thinner initial configuration to allow for decreased drying times. The reusable absorbent inserts may include a configurable pad and/or pad collection sleeve with multiple sections, each section including one or more layers. The configurable pad and pad collection sleeve may be made of the same or different materials or a combination of different materials. The pad collection sleeve may be made of textile materials or fabrics, fleece, terry, microterry, cotton, bamboo based, TENCEL, or combinations thereof. Durable, multiple layers may be fastened together such as through an overlock stitch, tape, glue, mechanical bonding, or like fastening items. The layers of the configurable pad may be made of textile materials or fabrics such as terry, microterry, cotton, bamboo based, TENCEL, or combinations thereof. In embodiments, the reusable absorbent inserts may be made of one or more fabric types, such as without limitation types provided through weaving, knitting, warp-knitting, crocheting, felting, or other nonwovens types. Some executions of fabric types via weaving, knitting, warp-knitting may include, and not be limited to, terry-cloth, waffle fabric, jacquard, jersey, 3D fabrics, and the like. Material types may include without limitation (1) natural fibers such as cotton, hemp, silk, wool, mineral, and the like; (2) man-made fibers such as polyester, polypropylene, re-constituted cellulose (such as viscose, Lyocell, TENCEL), and the like, or (3) combinations thereof, and/or may include (4) specialty fibers such as microfibers, hollow fibers, and the like. The sections may be folded upon each as described herein such that the layers are stacked upon each other in customizable layer configurations to form larger layer structures for greater absorbency in a small footprint to aid with decreased drying times after cleaning. In embodiments, may layers may be allocated to an area where additional absorbency is desired. In a final, folded configuration, allowing for integrity during usage such that the insert is secured after folded and will not unfold when being used, the reusable absorbent insert may include a length in a range of approximately 300 to 500 mm and a width in a range of approximately 80 to 120 mm. In embodiments, further fasteners may be utilized to maintain integrity after obtaining the final, folded configuration, such as snaps or VELCRO to secure the folded sections (e.g., zones) together. Thus, absorbency of such reusable absorbent inserts may be customized via the folded structures as described herein while the reusable absorbent structures stay fastened together while being folded without losing integrity. In embodiments, a contraction of a pouch opening (such as via a surrounding elastic material) of the pad configuration sleeve described herein into which the reusable absorbent insert is positioned in the folded position may aid to contain the folded reusable absorbent insert in the folded position without losing integrity and being prevented from unfolding. For example, the pouch sleeve may comprise an elastic material disposed proximate the pouch opening.

In the embodiments described herein, a base reusable absorbent insert may initially include 1-4 thin absorbent layers in an unfolded, flat-out configuration. The material may be made of existing or potential textiles, for example, but not limited to, cotton, terry, microterry, fleece, or the like. In the unfolded, flat-out configuration, the reusable absorbent insert can be divided into several zones as separate sections described herein and in greater detail further below. The separation of zones may be signaled (such as with sewing lines as folding guides via a threading) to facilitate the folding process. A user can fold the insert along the folding guides as described herein to suit the user's needs, which allows the user to adjust the size of a final, folded insert and/or its thickness distribution. For example, a user may double layer some areas where more absorbency is desired. In embodiments, indicia such as gender-specific indicia may be included to guide the user as an additional folding guide. To arrive at the final, folded configuration, and as described in greater detail below, a configurable pad of the insert such as in a semi-folded configuration may be collected into a container element of the insert attached to the base, which can take forms of, but not be limited to, a belt, a pocket, a pouch, or the like. The configurable pad of the insert may be collected into the container to form the final, folded configuration in various folding manners as described in greater detail with respect to the embodiments below, including, and not limited to, insertion into a container such as a pouch, being flipped inside out, or having the container flip inside out to at least partially cover a folded insert portion.

"Absorbent article" of the absorbent assemblies as described herein means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. Nonlimiting examples of absorbent articles are disclosed in U.S. Pat. Nos. 8,998,870, 9,089,456, 8,435,223, 9,011,402, 8,808,263, 8,759,605 and 8,932,273 and 9,078,789.

"Absorbent insert" and "insert" and "reusable absorbent insert" mean a component of a wearable absorbent article that is adapted to contain and/or absorb urine, feces, menses or any combination thereof, and is adapted to be installable and removable as a modular unit, from an outer shell of an absorbent assemble as described herein.

"Outer shell" or "outer cover" means a component of a wearable absorbent article as an absorbent assembly that is adapted to be worn about the lower torso of a wearer, and is adapted to support an absorbent insert and hold the insert close to the wearer's body. In various embodiments, the outer cover is reusable.

"Reusable," when referring to a component means that the component is adapted to be used for its intended purpose after initial use without substantial destruction of any portions of the component necessary for as-new functionality. For example, a reusable outer cover means an outer cover that is adapted to permit removal of at least a first insert, and replacement thereof with at least a second insert, without substantial destruction of any portions of the outer cover that are necessary to provide the substantial as-new functionality of the outer cover, and without the necessity of any repair or reconstruction following such insert replacement.

In aspects, and referring to FIGS. 1-4, an absorbent assembly 20 includes an outer shell 21 having a front portion 11 and a back portion 12 connected by an intermediate portion 14 forming a crotch region between a front waist region defined by the front portion 11 and a back waist region defined by the back portion 12. The outer shell 21 may include intermediate elastic strips 101 and 102 attached to the inner panel of FIG. 1 and outer panel of FIG. 2. Nonlimiting examples of outer shells are disclosed in U.S. Pat. Nos. 9,387,138 and 8,435,223.

The outer shell 21 and/or layers or portions thereof may be made of any durable or semi-durable knitted, woven or nonwoven textile or textile-like material that is appropriately compatible with skin of the intended wearer(s) and may include elastomeric materials. In embodiments, the reusable absorbent inserts 15 described herein and/or layers or portions thereof may be made of any durable or semi-durable knitted, woven or nonwoven textile or textile-like material that is appropriately compatible with skin of the intended wearer(s) and may include elastomeric material. The outer shell 21 may be formed of a single layer of a durable or semi-durable material, or may have two or more layers in the front region and/or rear region. Suitable examples are described in U.S. application Ser. Nos. 12/687,493; 12/687,412; 12/687,528; and 12/687,425 (all by Roe et al.). Nonlimiting examples of fibers, nonwovens and laminates of nonwovens and films that might be considered for use as semi-durable outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587. In some embodiments, the surfaces of both the interior, wearer-facing and exterior, garment-facing sides of the outer shell 21 may be formed from the same materials. However, due to different functional needs of the garment-facing surface and the wearer-facing surface, it may be desirable that the exterior surfaces comprise different materials.

In nonlimiting examples, the wearer-facing surface of the outer shell 21 may be formed from a first material or first combination of materials (collectively referred to as "first material" hereinafter). The material selected may include hydrophilic fibers, or fibers treated to be hydrophilic. This may be desired in some circumstances to cause the material forming wearer-facing surface to more readily absorb liquid or transmit liquid therethrough. This may serve to provide supplemental absorbency within the outer shell 21 for an event in which liquid exudates escape the insert, reducing the likelihood that the outer shell 21 will leak. Alternatively, it may provide one way of communicating to the user that liquid exudates have escaped the insert, by causing wetness to be transmitted through to the outer cover such that wetness is sensed by the wearer and/or visible on exterior surfaces. Alternatively, it may serve to provide a layer that tends to draw moisture away from the skin, for a drier, more comfortable feel. Additionally, or alternatively, it may be desirable to form the wearer-facing surface from an apertured material to facilitate transfer of exudates through the wear-facing surface and onto the absorbent insert. In some nonlimiting examples, the material may include fibers having hydrophobic properties, providing enhanced liquid containment attributes to the wearer-facing layer.

The garment-facing surface of the outer cover may be formed by a second material, or a second combination of materials (collectively referred to as "second material" hereinafter). The material selected may include fibers having hydrophobic properties, providing enhanced liquid containment attributes to such layer or may include a liquid impermeable material. In another example, however, it may be desirable in some circumstances for the selected material to include hydrophilic fibers, or fibers treated to be hydrophilic, so as will cause the material to more readily absorb liquid. This may serve to provide supplemental absorbency within the outer cover for the event in which liquid exudates escape the insert, or to provide one way of communicating to the user that liquid exudates have escaped the insert. Additionally, in some circumstances, it may be desirable that the material selected have soft tactile properties so as to have a pleasant feel that the user and/or wearer find attractive. The material also may be selected so as to have a desired appearance, including but not limited to coloration, sheen, and/or texture.

The first material and the second material may differ by one of the group consisting of: texture, caliper, elasticity, opacity, water resistance, absorbency, breathability and combinations thereof.

In nonlimiting examples, the outer shell 21 may be reversible such that both the surfaces are adapted to function as the wearer-facing surface and the garment-facing surface. This may provide, for example, variation in visible graphics or colors, textures and/or breathability against skin, liquid wicking properties and the like for the wearer. Layers or other elements of the outer shell 21 may be joined to each other via any suitable mechanism, including, for example, adhesives, mechanical bonding, ultrasonic bonding, sewing, stitching, serging, edging, and the like.

In nonlimiting examples, an elasticized waist feature of the outer shell 21 comprises elastic strands or ribbons joined to the nonwoven and/or textile layer(s). In further nonlimiting examples, the elasticized waist feature comprises a laminate of one or more textile and/or nonwoven layers and one or more elastomeric films. The elasticized waist element may comprise one or more rugosities if the elastic material is strained prior to lamination. In other nonlimiting examples, the layers of the elastic laminate may be joined at zero applied strain and subsequently activated. In alternative embodiments, the waist feature may be inelastic. In such configurations, the waist feature may provide additional anchoring about the waist of the wearer. In some embodiments, elastic elements are affixed within the outer shell 21 only at or near one or both of their respective ends, e.g., within a pouch, tube or envelope structure formed of outer cover material—referred to herein as a "drawstring elastic". The outer shell 21 may also include anchoring supplements, bands or systems thereof as described in more detail in U.S. Pat. No. 8,932,273.

Figure 3:
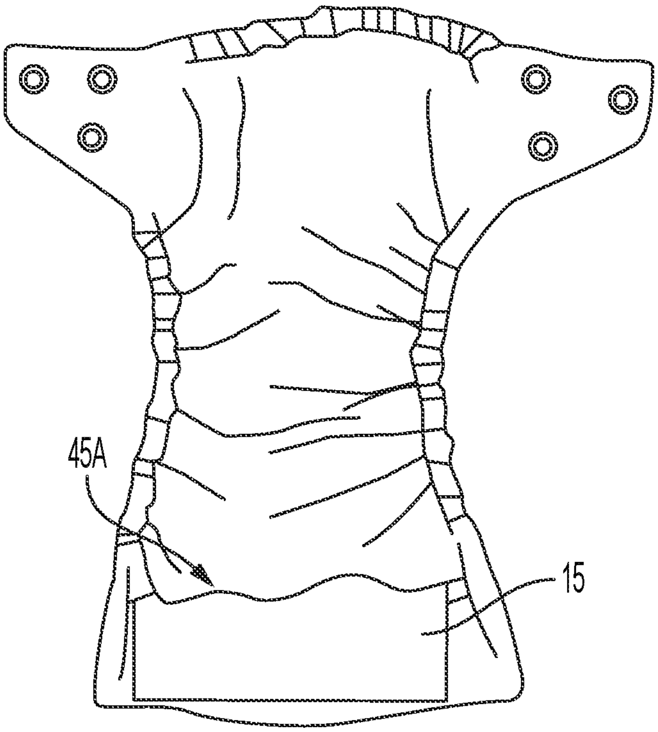
FIG. 3 is an interior side view of the absorbent assembly of FIG. 1, showing a reusable absorbent insert partially disposed in an interior pocket defined at an end of an outer shell of the absorbent assembly.
Figure 4:
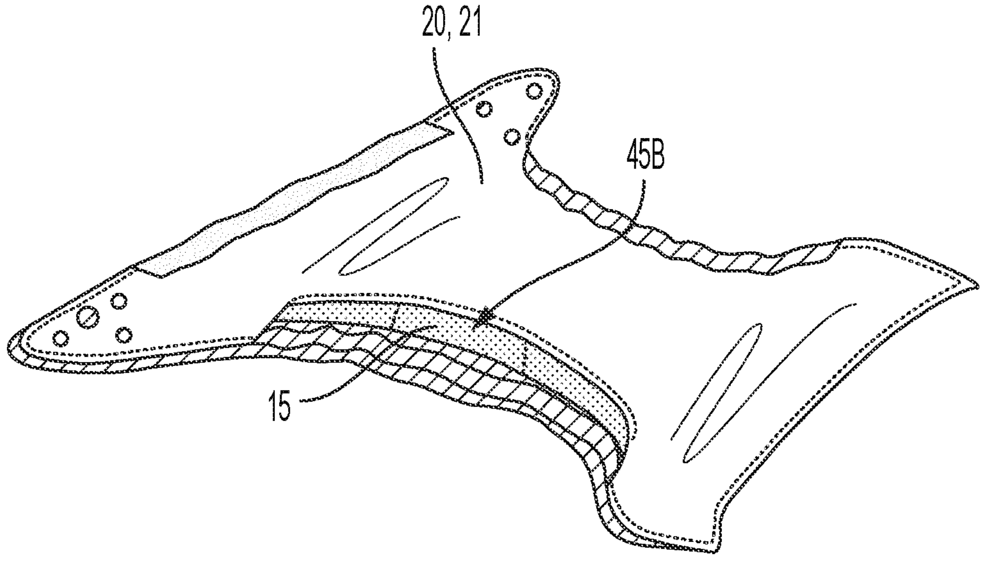
FIG. 4 is an interior side view of another absorbent assembly, showing a reusable absorbent insert partially disposed in an interior pocket defined at a side edge of an outer shell of the absorbent assembly, according to one or more embodiments shown and described herein.

Referring again to FIG. 1, an interior portion facing toward a wearer may include an opening 13 that defines an interior pocket 45A (FIG. 3) to receive a reusable absorbent insert 15 (FIG. 3). In the in-use configuration, the outer shell 21 may at least partially enclose the reusable absorbent insert 15 as shown in FIGS. 3-4, forming a pocket 45 in which the absorbent insert resides during use. In embodiments, the outer shell 21 may include a single layer including an inner, wearer-facing side on top of which the reusable absorbent inert 15 is positioned. As a non-limiting example, the reusable absorbent insert in FIG. 3 is shown partially disposed in the interior pocket 45A defined at an end in the front portion 11 of the outer shell of the absorbent assembly. The interior pocket 45A may be defined any location within the inner panel, including and not limited to, for example, an end in the back portion 12, alongside edges (as shown by interior pocket 45B of FIG. 4), in central portions, or at other portions of the inner panel within which the reusable absorbent insert 15 may be received. In embodiments, the inner panel may be a fleece material made of polyester or like materials. As described in greater detail further below, the reusable absorbent insert 15 may be made of multiple layers of cotton or reusable pads.

Figure 2:
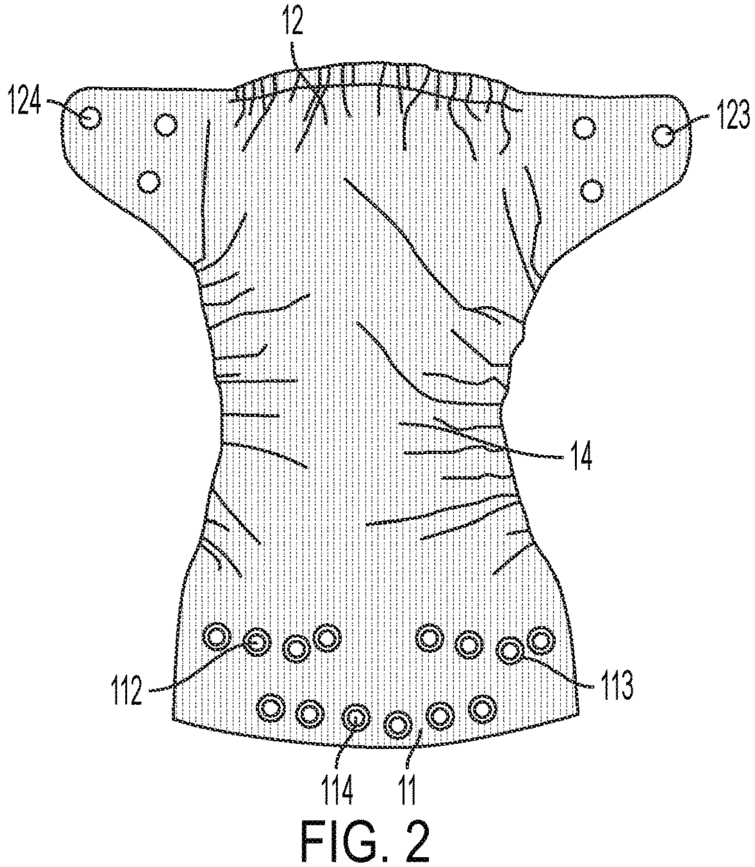
FIG. 2 is an exterior side view of the absorbent assembly of FIG. 1, showing an exterior portion that faces away from the wearer.

FIG. 2 shows an exterior portion of the outer shell that faces away from the wearer. Fasteners 123 and 124 of elongated wings 126 and 127 (FIG. 1) of the back portion 12 are configured to fasten to fasteners 112, 113, and 114 of the front portion 11 when the outer shell is in a folded, fastened configuration for the wearer. In embodiments, the fasteners may be snaps or other suitable fastening mechanisms. Non-limiting examples of engageable fastening and receiving components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274.

As noted above, in the in-use configuration of the present invention, the outer shell 21 at least partially encloses the absorbent insert 15, forming a pocket 45 in which the absorbent insert resides during use. The wearer-facing surface of the outer shell 21 may cover at least about 60%, or at least about 75% or at least about 80%, or at least about 90%, or from about 60% to about 100% of the surface area of the absorbent insert 15, when the absorbent insert 15 is fully positioned within the pocket 45 as designed, reciting for said range every 5% increment therein. In some nonlimiting examples, the width of the outer shell 21 wearer-facing surface is greater than the width of the absorbent insert 15 throughout a majority of, or all of, the length of the absorbent insert. Additionally, or alternatively, the garment-facing surface of the outer shell 21 may cover at least about 60%, or at least about 75% or at least about 80%, or at least about 90%, or from about 60% to about 100% of the surface area of the absorbent insert 15, when the absorbent insert 15 is fully positioned within the pocket 45 as designed, reciting for said range every 5% increment therein. In some nonlimiting examples, the width of the outer shell 21 garment-facing surface is greater than the width of the absorbent insert 15 throughout a majority of, or all of, the length of the absorbent insert 15.

The outer shell 21 comprises one or more openings 13 which are capable of receiving an absorbent insert 15, as shown in FIGS. 1 and 3-4. The openings 13 are sized and shaped to permit the absorbent insert 15 to be inserted into the pocket 45 by the user. In various embodiments, an opening 13 comprises a maximum longitudinal length, Lo, that is at least about 50%, or at least about 60%, or at least about 70%, or from about 50% to about 100%, or from about 55% to about 85%, or from about 60% to about 75% of the length of the outer shell 21, Lc, reciting for each range every 5% increment therein.

The one or more openings 13 may include at least one longitudinally-extending opening defining a pocket such as interior pocket 45B (FIG. 4). By longitudinally-extending, it is meant that the opening extends more in the longitudinal dimension than in the lateral dimension. For purposes of longitudinally-extending, the longitudinal direction includes directions within 40 degrees of the maximum linear dimension in the x-y plane of the outer shell 21. The longitudinally-extending opening may be present in the crotch region. The longitudinally-extending opening may extend into one or both of the front and rear regions.

The opening 13 may be sized and shaped such that the absorbent insert 15 will remain in the interior pocket 45 once inserted. For example, the opening 13 may be smaller in one or more dimensions than the insert 15. Additionally, or alternatively, a second edge of the opening 13 may be spaced from the edge of the opening 13 such that less than 10 mm of void space in the z-direction exists above or below the absorbent insert 15 within the pocket 45.

The opening 13 may be sealable, such that it may be closed or repeatedly opened and reclosed. In nonlimiting examples, the first edge and/or the second edge may include means for attaching to each other, including any of the fastening components and/or receiving components described above, as well as pressure sensitive adhesive. Additionally, or alternatively, the first or second edge may be capable of wrapping about the longitudinal edge and being secured to an exterior surface.

Referring again to FIGS. 3-4, the reusable absorbent insert 15 may be designed to contain and/or absorb body exudates, and may be made of pliable materials as will be described further below. The reusable absorbent insert 15 may be made of washable material such as cloth, or of a material suitable for composting, such as cellulose. In other embodiments, the absorbent insert may be disposable an made from materials commonly found in disposable absorbent articles. The reusable absorbent insert 15 may have a topsheet and a backsheet that may be joined together. An absorbent core may be disposed between the topsheet and the backsheet.

The topsheet is generally a portion of the insert 15 that may be positioned at least in partial contact or close proximity to a wearer. Suitable topsheets may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet is generally supple, soft feeling, and non-irritating to a wearer's skin. Generally, at least a portion of the topsheet is liquid pervious, permitting liquid to readily penetrate through the thickness of the topsheet. The topsheet may comprise one or more apertures.

Any portion of the topsheet may be coated with a lotion, antibacterial or skin care composition as is known in the art. The topsheet may be fully or partially elasticized or may be foreshortened so as to provide a void space between the topsheet and the core. Topsheet, backsheet or any portion of the topsheet or backsheet may be embossed and/or matte finished to provide a more cloth-like appearance.

Backsheet is generally the outer liner portion of insert 15 forming the garment-facing surface thereof, and prevents the exudates absorbed and contained within insert 15 from wicking through and soiling the outer shell 21. The backsheet may comprise one or more nonwovens, films, elastomeric films, foams, strands, or combinations of these or other suitable materials with nonwovens or synthetic films. In nonlimiting examples, the backsheet is a laminate of an elastomeric material, such as a film, and a nonwoven.

In various embodiments, the backsheet is substantially water-impermeable. Suitable backsheet materials include nonwovens and/or films. Other suitable backsheet materials may include breathable materials that permit vapors to escape from the insert 15 while still preventing exudates from passing through the backsheet. Exemplary breathable materials may include materials such as woven webs, nonwoven webs, composite materials such as film-coated nonwoven webs, and microporous films.

Other suitable materials and/or manufacturing techniques may be used to provide a suitable backsheet including, but not limited to, surface treatments, particular film selections and processing, particular filament selections and processing. Backsheet may be joined to topsheet, absorbent core or any other element of insert 15 by any suitable attachment mechanism known in the art. For example, the attachment mechanism may include a continuous line or layer of adhesive, a patterned layer of adhesive, or an array of separate lines, spirals, or spots of adhesive.

As described above, the insert 15 may have an absorbent core disposed within an envelope-like structure formed by the topsheet and backsheet. The absorbent core may comprise materials suitable for absorbency and for washing and reuse of the insert. In nonlimiting examples, the insert 15 may be formed of cotton, fleece, flannel, felt, nylon, polyester, terry cloth and combinations thereof.

FIGS. 5A-11F show various embodiments of the reusable absorbent insert 15 as described herein. In embodiments, the reusable absorbent insert 15 includes a configurable pad 200 and a pad collection sleeve 204, 206. The pad collection sleeve 204, 206 may comprise an elastomeric material. The configurable pad 200 may include multiple layers fastened together through a fastening mechanism 202, such as an overlock stitch, adhesive, or other suitable fastening items.

Figure 5A:
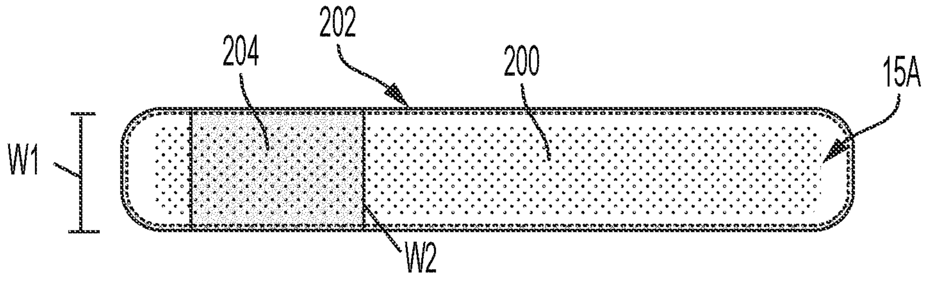
FIG. 5A is elevation top plan view of a reusable absorbent insert including a pad collection sleeve having a belt with two open ends, according to one or more embodiments shown and described herein.
Figure 5B:
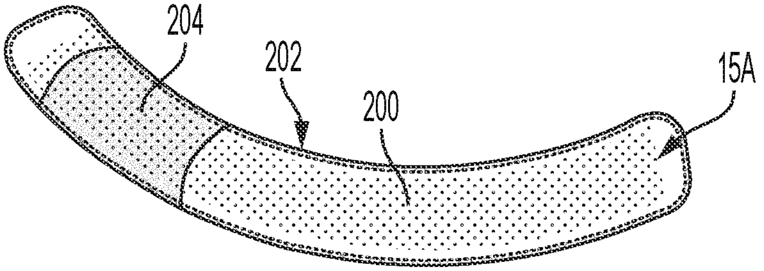
FIG. 5B is a top view of the reusable absorbent insert of FIG. 5A in a curved position.
Figure 6A:
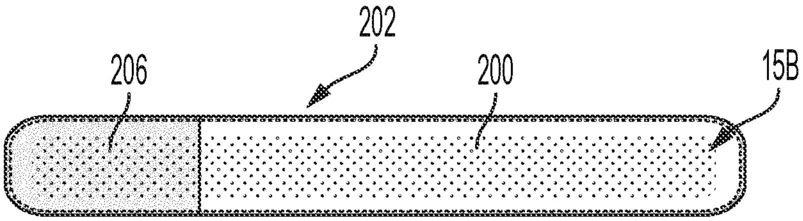
FIG. 6A is elevation top plan view of a reusable absorbent insert including a pad collection sleeve having a pocket with a closed end, according to one or more embodiments shown and described herein.
Figure 6B:
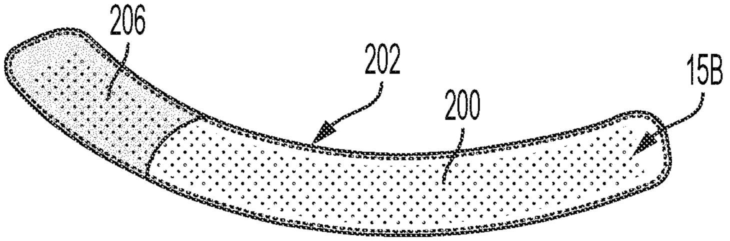
FIG. 6B is a top view of the reusable absorbent insert of FIG. 6A in a curved position.
Figure 7A:
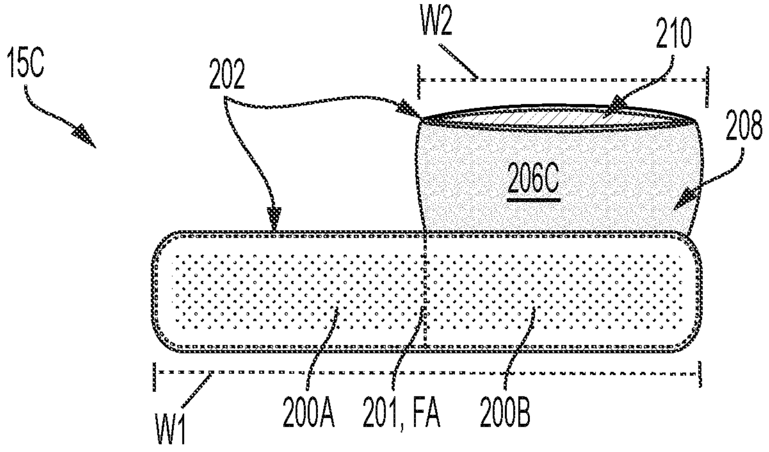
FIG. 7A is a schematic view of another embodiment of a reusable absorbent insert in an unfolded, flat-out configuration, according to one or more embodiments shown and described herein.

The configurable pad 200 may include, as shown in at least FIG. 7A as a non-limiting example, a first section 200A and a second section 200B, the second section 200B separated from the first section 200A at least partially by a folding guide 201. In embodiments, the folding guide 201 may be formed by a threading to separate the sections 200A, 200B. As shown in FIGS. 5A and 7A as non-limiting examples, and as applicable to the embodiments of FIGS. 5A-11F described herein, the configurable pad 200 may have an unfolded pad plan surface area comprising an unfolded pad width W1 when the reusable absorbent insert 15 is in an unfolded, flat-out configuration. The pad collection sleeve 206 may have an unfolded sleeve plan surface area comprising an unfolded sleeve width W2 when the reusable absorbent insert 15 is in an unfolded, flat-out configuration. The unfolded pad width W1 is greater than or substantially equal to the unfolded sleeve width W2. As described above, the reusable absorbent insert 15 is configured to be inserted into an interior pocket 45, 45A, 45B of an outer shell 21 of an absorbent assembly 20.

In the embodiments of FIGS. 7A-11F, and as described in greater detail further below, a method of folding a reusable absorbent insert 15 may include folding a first section 200A of a configurable pad 200 over a second section 200B of the configurable pad 200 along a folding axis FA of a folding guide 201 to form a semi-folded configuration, the folding guide 201 at least partially separating the second section 200B from the first section 200A. As described above, the configurable pad 200 has an unfolded pad plan surface area that has an unfolded pad width W1 (see FIG. 7A) when the reusable absorbent insert 15 is in an unfolded, flat-out configuration, the semi-folded configuration has a semi-folded pad width W3 (see FIG. 8C), and the folding axis FA is transverse to the unfolded pad width W1 and the semi-folded pad width W3. The method may further include folding a pad collection sleeve 206 along an axis 203 (see FIG. 8C) parallel to the semi-folded pad width W3 into a folded, final configuration that at least partially covers the configurable pad 200. As described above, the pad collection sleeve 206 has an unfolded sleeve plan surface area that has an unfolded sleeve width W2 (see FIG. 7A) when the reusable absorbent insert 15 is in an unfolded, flat-out configuration, the unfolded pad width W1 being greater than or substantially equal to the unfolded sleeve width W2 and substantially equal to the semi-folded pad width W3 (see FIG. 8C).

Referring again to FIGS. 5A-5B, a reusable absorbent insert 15A is shown including a pad collection sleeve 204 having a belt with two open ends through which the configurable pad 200 is received. In embodiments, the configurable pad 200 may be folded along a latitude direction and inserted into the belt of the pad collection sleeve 204. As a non-limiting example, the pad collection sleeve 204 may include a pair of opposing side edges and a pair of opposing end edges. At least a portion of each of the pair of opposing side edges may be fastened to a portion of the configurable pad 200, such as via the fastening mechanism 202, and the pair of opposing end edges defining the unfolded sleeve width W2 when the reusable absorbent insert 15 is in an unfolded, flat-out configuration may be free of attachment to the configurable pad 200.

FIGS. 6A-6B show a reusable absorbent insert 15B including a pad collection sleeve 206 a pocket with a closed end and an open end through which the configurable pad 200 is received. In embodiments, the configurable pad 200 may be folded along a latitude direction and inserted into the pocket of the pad collection sleeve 206. The pad collection sleeve 206 may include a pair of opposing side edges and a pair of opposing end edges defining the unfolded sleeve width W2 when the reusable absorbent insert 15 is in an unfolded, flat-out configuration. At least a portion of each of the pair of opposing side edges is fastened such as via fastening mechanism 202 to a portion of the configurable pad 200, and at least a portion of one of the pair of opposing end edges is attached to a portion of the configurable pad 200, and one of the pair of opposing end edges is free of attachment to the configurable pad 200.

In the embodiment of FIGS. 7A-7D, a first section 200A of the configuration pad 200 may be folded along a latitude direction over a second section 200B and then collected into a pocket of the pad collection sleeve 206C by flipping the pocket inside out and over the folded configuration pad 200, as described in greater detail below. FIG. 7A shows a reusable absorbent insert 15C in an unfolded, flat-out configuration. As shown in FIG. 7A, and similarly FIGS. 9A and 10A described in greater detail further below, an exterior portion of the pad collection sleeve 206C when the reusable absorbent insert is in an unfolded, flat-out configuration is fastened via a fastening mechanism 202 to at least a portion of the configurable pad 200. In embodiments, the at least a portion of the configurable pad 200 is part of the second section 200B of the configurable pad 200. The fastening mechanism 202 may be an overlock stitch, a flat seam, an adhesive or combinations thereof.

Figure 7B:
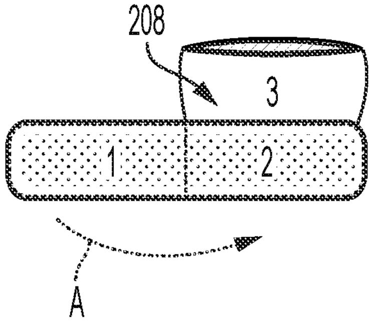
FIG. 7B is a schematic view of the reusable absorbent insert of FIG. 7A in a folding configuration.
Figure 7C:
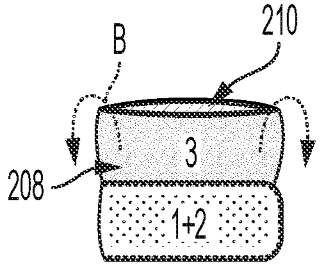
FIG. 7C is a schematic view of the reusable absorbent insert of FIG. 7A in a semi-folded configuration.
Figure 7D:
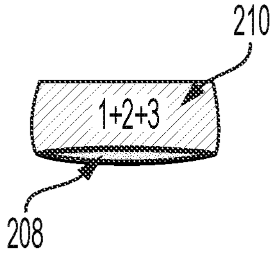
FIG. 7D is a schematic view of the reusable absorbent insert of FIG. 7A in a folded, final configuration.

FIG. 7B shows the reusable absorbent insert 15C of FIG. 7A in a folding configuration in which the first section 200A (1) of the configurable pad 200 is configured to fold in the direction of arrow A over the folding guide 201 onto the second section 200B (2) of the configurable pad 200. FIG. 7C shows the reusable absorbent insert 15C in a semi-folded configuration in which the first section 200A of the configurable pad 200 is folded over the folding guide 201 onto the second section 200B of the configurable pad 200 to form a combination section (1+2) in the semi-folded configuration. The pad collection sleeve 206C (3) is then configured to fold down along the direction of arrows B over the combination section (1+2) to arrive at the folded, final configuration of FIG. 7D. FIG. 7D shows the reusable absorbent insert 15C in the folded, final configuration defining a combination layering (1+2+3).

In the embodiments described herein, the pad collection sleeve 204, 206 comprises an exterior portion 208 that is exterior facing and an interior portion 210 that is interior facing when the reusable absorbent insert 15 is in an unfolded, flat-out configuration. In aspects, the exterior portion 208 may be made of a fleece layer, and the interior portion 210 may be a pouch interior or opening. As shown in the embodiment of FIGS. 7A-7D as a non-limiting example, when the reusable absorbent insert 15C is in a folded, final configuration, the interior portion 210 is folded over the configurable pad 200 and is exterior facing. Alternatively, as shown in FIGS. 8A-8D as a non-limiting example, and as described in greater detail below, when the reusable absorbent insert is in a folded, final configuration, the configurable pad 200 is folded such as upward into the interior portion 210 that is interior facing.

Figure 8A:
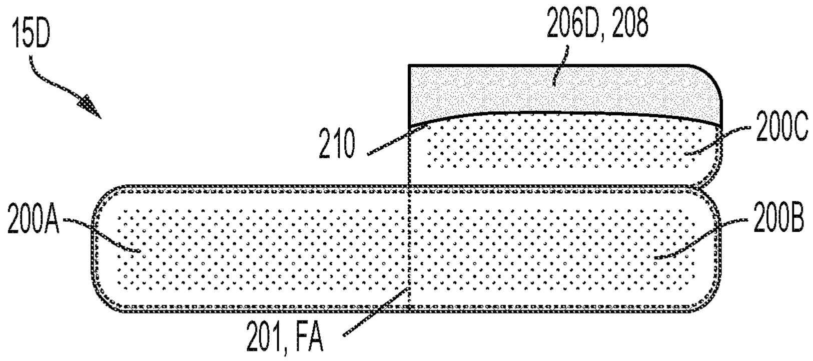
FIG. 8A is a schematic view of another embodiment of a reusable absorbent insert in an unfolded, flat-out configuration, according to one or more embodiments shown and described herein.
Figure 8B:
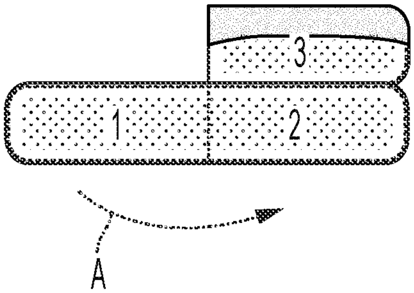
FIG. 8B is a schematic view of is a schematic view of the reusable absorbent insert of FIG. 8A in a folding configuration.
Figure 8C:
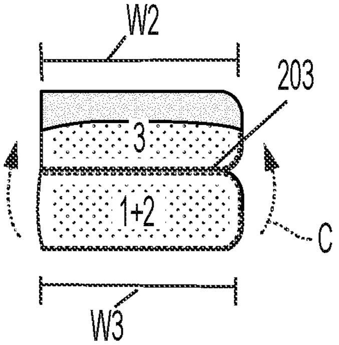
FIG. 8C is a schematic view of the reusable absorbent insert of FIG. 8A in a semi-folded configuration.

In embodiments, such as shown in FIGS. 8A-9D, the folding guide 201 (see FIG. 8A) includes a folding axis FA transverse to the unfolded sleeve width W2 (see FIG. 8C). In the embodiment of FIGS. 8A-8D, a first section 200A of the configuration pad 200 may be folded along a latitude direction over a second section 200B, then folded along a longitudinal direction over a third section 200C and collected into a pocket of the pad collection sleeve 206D, as described in greater detail below. The third section 200C may be part of the pocket of the pad collection sleeve 206D including an absorbent material.

Figure 8D:
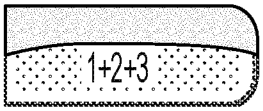
FIG. 8D is a schematic view of the reusable absorbent insert of FIG. 8A in a folded, final configuration.

FIG. 8A shows a reusable absorbent insert 15D in an unfolded, flat-out configuration including a configurable pad 200 having a first section 200A (1), a second section 200B (2), and a third section 200C (3). FIG. 8B shows the reusable absorbent insert 15D in a folding configuration, FIG. 8C shows the reusable absorbent insert 15D in a semi-folded configuration in which the first section 200A is folded onto the second section 200B to form combination section (1+2), and FIG. 8D shows the reusable absorbent insert 15D in a folded, final configuration in which combination section (1+2) is folded onto the third section 200C) to form a folded combination section (1+2+3). Referring to FIG. 8B as a non-limiting example, the first section 200A is configured to fold along the folding guide 201 and over the folding axis FA in the direction of arrow A to cover the second section 200B to form a semi-folded configuration. The semi-folded configuration includes a semi-folded pad width W3 as shown in FIG. 8C that is substantially equal to the unfolded sleeve width W2. Referring to FIG. 8C, the configurable pad 200 in the semi-folded configuration is configured to further fold such as upwards in the direction of arrows C along an axis 203 parallel to the unfolded sleeve width W2 to tuck into an interior portion of the pad collection sleeve 206D to form the folded, final configuration of FIG. 8D. In the folded, final configuration of FIG. 8D, the folded combination section (1+2+3) of the configurable pad 200 is at least partially covered by the pad collection sleeve 206D.

Figure 9A:
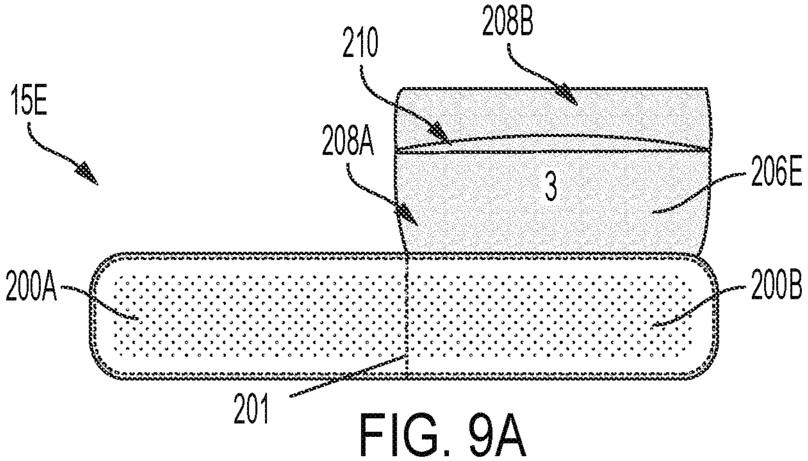
FIG. 9A is a schematic view of another embodiment of a reusable absorbent insert in an unfolded, flat-out configuration, according to one or more embodiments shown and described herein.
Figure 9B:
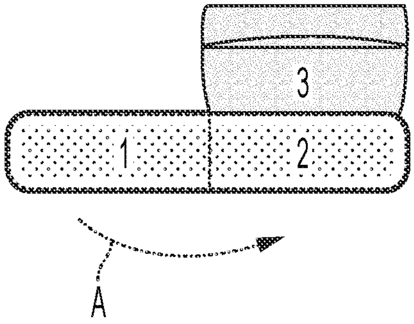
FIG. 9B is a schematic view of the reusable absorbent insert of FIG. 9A in a folding configuration.
Figure 9C:
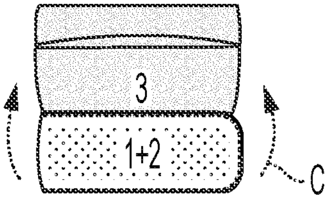
FIG. 9C is a schematic view of the reusable absorbent insert of FIG. 9A in a semi-folded configuration.
Figure 9D:
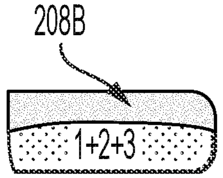
FIG. 9D is a schematic view of the reusable absorbent insert of FIG. 9A in a folded, final configuration.

In the embodiment of FIGS. 9A-9D, a first section 200A of the configuration pad 200 may be folded along a latitude direction over a second section 200B, then folded along a longitudinal direction to be collected into a pocket of the pad collection sleeve 206E, as described in greater detail below. FIG. 9A shows a reusable absorbent insert 15E in an unfolded, flat-out configuration, FIG. 9B shows the reusable absorbent insert 15E in a folding configuration, FIG. 9C shows the reusable absorbent insert 15E in a semi-folded configuration, and FIG. 9D shows the reusable absorbent insert 15E in a folded, final configuration. The first section 200A (1) of the configurable pad 200 of FIGS. 9A-9B is configured to fold along the folding guide 201 and over the folding axis to cover the second section 200B (2) to form the semi-folded configuration shown in FIG. 8C. The semi-folded configuration includes a semi-folded pad width W3 that is substantially equal to the unfolded sleeve width W2. The configurable pad in the semi-folded configuration forms a combination section (1+2) and is configured to further fold along an axis 203 parallel to the unfolded sleeve width W2 upward in the direction of arrows C to fold over the exterior portion 208A and tuck into the interior portion 210 of the pad collection sleeve 206E. In the folded, final configuration of FIG. 9D, a folded combination section (1+2+3) is formed that is at least partially covered by, for example, the exterior portion 208B of the pad collection sleeve 206E in the folded, final configuration.

In the embodiment of FIGS. 10A-10G, a first section 200A1 of the configuration pad 200 is disposed below a second section 200B and including a fastened portion FP to fasten to the second section 200B and a non-fastened portion NFP to be folded in a latitude direction over the fastened portion FP. Once folded, the first section 200A1 may then be folded along a longitudinal direction over the second section 200B, and then then collected into a pocket of the pad collection sleeve 206E by flipping the pocket inside out and over to at least partially cover the folded configuration pad 200, as described in greater detail below, as described in greater detail below. While one non-fastened portion is shown that may define a slit as described below, it is to be understood and is within the scope of this disclosure that embodiments may include multiple non-fastened portions in a single section or multiple sections to allow for multiple folding configuration.

Figure 10A:
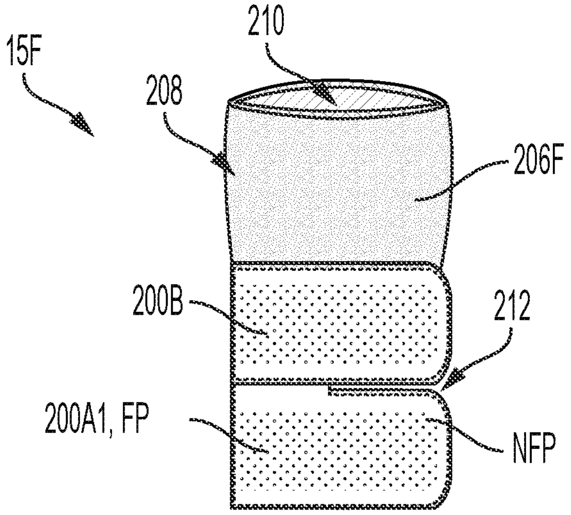
FIG. 10A is a schematic view of another embodiment of a reusable absorbent insert in an unfolded, flat-out configuration, according to one or more embodiments shown and described herein.
Figures 10B, 10C, 10D:
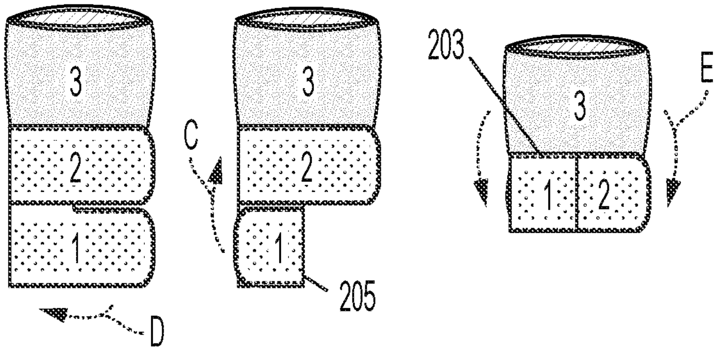
FIG. 10B is a schematic view of the reusable absorbent insert of FIG. 10A in a folding configuration.
FIG. 10C is a schematic view of the reusable absorbent insert of FIG. 10A in a first semi-folded configuration.
FIG. 10D is a schematic view of the reusable absorbent insert of FIG. 10A in a second semi-folded configuration.
Figures 10E, 10F, 10G:
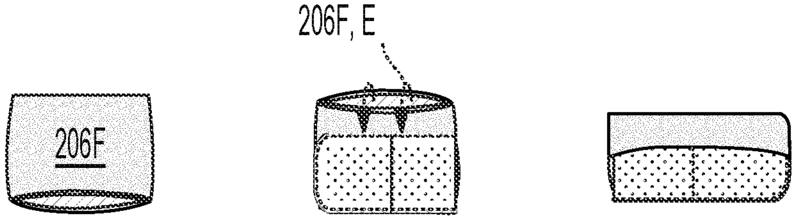
FIG. 10E is a schematic view of the reusable absorbent insert of FIG. 10A in a folded, final configuration.
FIG. 10F is a schematic view of a view of another side of another embodiment of the reusable absorbent insert of FIG. 10A in a semi-folded configuration.
FIG. 10G is a schematic view of the reusable absorbent insert of FIG. 10F in another folded, final configuration.

FIG. 10A shows a reusable absorbent insert 15F in an unfolded, flat-out configuration, FIG. 10B shows the reusable absorbent insert 15F in a folding configuration, FIG. 10C shows the reusable absorbent insert 15F in a first semi-folded configuration, FIG. 10D shows the reusable absorbent insert 15F in a second semi-folded configuration, and FIG. 10E shows the reusable absorbent insert 15F in a folded, final configuration in which the configurable pad 200 forming a folded combination section is fully covered by the pad collection sleeve in the folded, final configuration. FIG. 10F shows another side compared to FIG. 10D of another embodiment of the reusable absorbent insert 15F in a semi-folded configuration, and FIG. 10G shows the reusable absorbent insert 15F of FIG. 10E in another folded, final configuration in which the configurable pad 200 forming a folded combination section is at least partially covered by the pad collection sleeve in the folded, final configuration.

Referring to FIGS. 10A and 10C, a first section 200A1 (1) of the configurable pad comprises a non-fastened portion NFP, a fastened portion FP, and a secondary folding guide 205 defined at an interior end of the non-fastened portion NFP. The non-fastened portion may further define a slit 212 with the interior end and the second section 200B. The secondary folding guide 205 includes a secondary folding axis transverse to the unfolded sleeve width W2, and the first section 200A1 (1) is configured to fold along the secondary folding guide 205 in the direction of arrow D (FIG. 10B) and over the secondary folding axis to form a semi-folded first section configuration as shown in FIG. 10C.

The first section 200A1 (1) is fastened to the second section 200B (2) via the fastened portion FP and is configured to fold over the fastened portion FP in a direction parallel to the unfolded sleeve width W2 in the direction of arrow C as shown in FIG. 10C to cover at least a portion of the second section 200B (2) to form a semi-folded second section configuration as shown in FIG. 10D. The configurable pad 200 in the semi-folded second section configuration of FIG. 10D is configured to further fold along an axis 203 parallel to the unfolded sleeve width W2 downward along the direction of arrows E into a folded, final configuration and be at least partially covered by the pad collection sleeve 206F in the folded, final configuration. The folded, final configuration of FIG. 10E shows the configurable pad 200 being fully covered by the pad collection sleeve 206F. Alternatively, the folded, final configuration of FIG. 10G shows the configurable pad 200 being partially covered by the pad collection sleeve 206F after the reusable absorbent insert 15F of FIG. 10F in a semi-folded configuration is folded into the folded, final configuration of FIG. 10G.

Figure 11A:
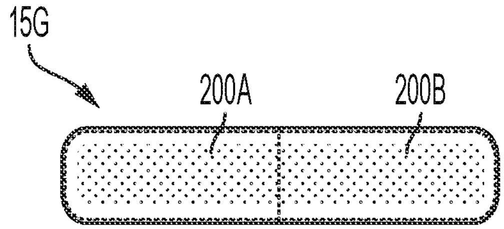
FIG. 11A is a schematic view of another embodiment of a first side of a reusable absorbent insert in an unfolded, flat-out configuration, according to one or more embodiments shown and described herein.
Figure 11B:
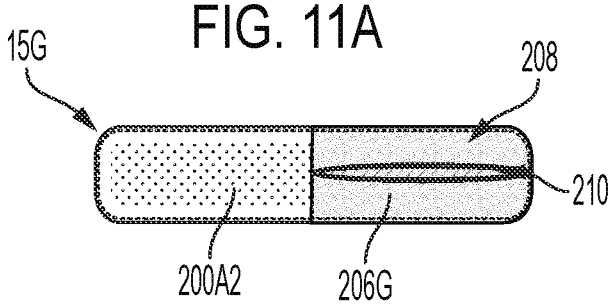
FIG. 11B is a schematic view of a second side of the reusable absorbent insert of FIG. 11A in the unfolded, flat-out configuration.
Figure 11C:
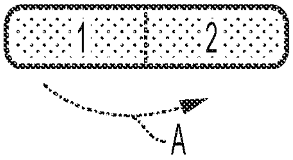
FIG. 11C is a schematic view of the first side of the reusable absorbent insert of FIG. 11A in a folding configuration.
Figure 11D:
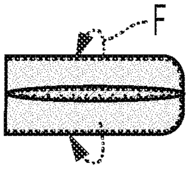
FIG. 11D is a schematic view of the second side of the reusable absorbent insert of FIG. 11A and as shown in FIG. 11B in a first semi-folded configuration.
Figure 11E:
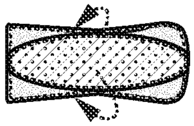
FIG. 11E is a schematic view of the second side of the reusable absorbent insert of FIG. 11A and as shown in FIG. 11B in a second semi-folded configuration.
Figure 11F:
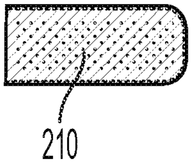
FIG. 11F is a schematic view of the second side of the reusable absorbent insert of FIG. 11A and as shown in FIG. 11B in a folded, final configuration, according to one or more embodiments shown and described herein.

In the embodiment of FIGS. 11A-11F, a first section 200A of the configuration pad 200 may be folded on a first side along a latitude direction over a second section 200B, and then a pocket of the pad collection sleeve 206G on an opposite side may be flipped inside out to contain the finished and folded configuration pad 200 of the reusable absorbent insert 15G, as described in greater detail below. FIG. 11A shows a first side of a reusable absorbent insert 15G in an unfolded, flat-out configuration, the first side including the first section 200A and the second section 200B. FIG. 11B shows a second side of the reusable absorbent insert 15G in the unfolded, flat-out configuration in which the pad collection sleeve 206 includes an exterior portion 208 that is exterior facing and interior portion 210 that is interior facing. The second side (FIG. 11B) includes an opposing first section 200A2 disposed on the opposite side of the first section 200A and the pad collection sleeve 206G disposed on the opposite side of the second section 200B. To arrive in a semi-folded configuration of FIG. 11D (showing the second side of FIG. 11B in the semi-folded configuration), the configurable pad 200 is folded along the folding guide 201 on the first side (as shown in FIGS. 11A and 11C) in the direction of arrow A. The configurable pad 200 in the semi-folded configuration of FIG. 11D (not shown) is disposed on the first side (shown in FIG. 11A) of the pad collection sleeve 206G, and a second side of the pad collection sleeve 206G is further configured to fold out and over the configurable pad 200 in the semi-folded configuration in the direction of arrows F such that the exterior portion 208 wraps around to turn inside out and thus folds over to become interior facing and the interior portion 210 becomes partially exterior facing as shown in FIG. 11E. The exterior portion 208 continues to fold over to finally form into a folded, final configuration of FIG. 11F in which the interior portion 210 if fully exterior facing to at least partially cover the configurable pad 200 in the folded, final configuration. As a non-limiting example, FIG. 11C shows the first side of the reusable absorbent insert 15G in a folding configuration, FIG. 11D shows the second side of the reusable absorbent insert 15G of FIG. 11B in a first semi-folded configuration, FIG. 11E shows the second side of the reusable absorbent insert 15G of FIG. 11B in a second semi-folded configuration, and FIG. 11F shows the second side of the reusable absorbent insert 15G of FIG. 11B in a folded, final configuration in which the interior portion 210 is exterior facing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A reusable absorbent insert, comprising:

a configurable pad, the configurable pad comprising a first section and a second section, the second section separated from the first section at least partially by a folding guide; and a pad collection sleeve;

wherein the configurable pad has an unfolded pad plan surface area comprising an unfolded pad width when the reusable absorbent insert is in an unfolded, flat-out configuration;

wherein the pad collection sleeve has an unfolded sleeve plan surface area comprising an unfolded sleeve width when the reusable absorbent insert is in an unfolded, flat-out configuration;

wherein the unfolded pad width is greater than or substantially equal to the unfolded sleeve width; and wherein the first section comprises a non-fastened portion, a fastened portion, and a secondary folding guide defined at an interior end of the non-fastened portion, the secondary folding guide comprises a secondary folding axis transverse to the unfolded sleeve width, and the first section is configured to fold along the secondary folding guide and over the secondary folding axis to form a semi-folded first section configuration.

2. The reusable absorbent insert of claim 1, wherein the reusable absorbent insert is configured to be inserted into an interior pocket of an outer shell of an absorbent assembly.

3. The reusable absorbent insert of claim 1, wherein the pad collection sleeve comprises elastomeric material.

4. The reusable absorbent insert of claim 1, wherein the pad collection sleeve comprises a belt with two open ends or a pocket with a closed end.

5. The reusable absorbent insert of claim 1, wherein an exterior portion of the pad collection sleeve when the reusable absorbent insert is in an unfolded, flat-out configuration is fastened via a fastening mechanism to at least a portion of the configurable pad.

6. The reusable absorbent insert of claim 5, wherein the at least the portion of the configurable pad comprises the second section of the configurable pad, and the fastening mechanism comprises an overlock stitch, a flat seam, an adhesive or combinations thereof.

7. The reusable absorbent insert of claim 1, wherein the pad collection sleeve comprises an exterior portion that is exterior facing and an interior portion that is interior facing when the reusable absorbent insert is in an unfolded, flat-out configuration.

8. The reusable absorbent insert of claim 7, wherein, when the reusable absorbent insert is in a folded, final configuration, the interior portion is folded over the configurable pad and is exterior facing.

9. The reusable absorbent insert of claim 7, wherein, when the reusable absorbent insert is in a folded, final configuration, the configurable pad is folded into the interior portion that is interior facing.

10. The reusable absorbent insert of claim 1, wherein the folding guide comprises a folding axis parallel to the unfolded sleeve width, and the first section is configured to fold along the folding guide and over the folding axis to cover the second section to form a semi-folded second section configuration, the semi-folded second section configuration comprising a semi-folded pad width, the semi-folded pad width substantially equal to the unfolded sleeve width.

11. The reusable absorbent insert of claim 10, wherein the configurable pad in the semi-folded second configuration is configured to further fold along an axis parallel to the unfolded sleeve width into a folded, final configuration and be at least partially covered by the pad collection sleeve in the folded, final configuration.

12. The reusable absorbent insert of claim 10, wherein the configurable pad in the semi-folded second configuration is disposed on a first side of the pad collection sleeve, and a second side of the pad collection sleeve is further configured to fold over the configurable pad in the semi-folded second configuration into a folded, final configuration to at least partially cover the configurable pad in the folded, final configuration.

13. The reusable absorbent insert of claim 1, wherein the first section is fastened to the second section via the fastened portion and is configured to fold over the fastened portion in a direction parallel to the unfolded sleeve width to cover at least a portion of the second section to form a semi-folded second section configuration.

14. The reusable absorbent insert of claim 13, wherein the configurable pad in the semi-folded second section configuration is configured to further fold along an axis parallel to the unfolded sleeve width into a folded, final configuration and be at least partially covered by the pad collection sleeve in the folded, final configuration.

15. An absorbent assembly, comprising:

an outer shell comprising a first layer of material and a second layer of material, the outer shell defining an interior pocket at least partially between the first layer of material and the second layer of material; and a reusable absorbent insert configured to be received in the interior pocket of the outer shell of the absorbent assembly, the reusable absorbent insert comprising:

a configurable pad, the configurable pad comprising a first section and a second section, the second section separated from the first section at least partially by a folding guide; and a pad collection sleeve;

wherein the configurable pad has an unfolded pad plan surface area comprising an unfolded pad width when the reusable absorbent insert is in an unfolded, flat-out configuration;

wherein the pad collection sleeve has an unfolded sleeve plan surface area comprising an unfolded sleeve width when the reusable absorbent insert is in an unfolded, flat-out configuration;

wherein the unfolded pad width is greater than or substantially equal to the unfolded sleeve width;

wherein the pad collection sleeve comprises an interior portion that is interior facing when the reusable absorbent insert is in an unfolded, flat-out configuration; and wherein, when the reusable absorbent insert is in a folded, final configuration, the interior portion is folded over the configurable pad and is exterior facing.

16. The absorbent assembly of claim 15, wherein the pad collection sleeve comprises an exterior portion that is exterior facing when the reusable absorbent insert is in an unfolded, flat-out configuration.

17. The absorbent assembly of claim 16, wherein the configurable pad is folded into the interior portion that is interior facing.

18. A method of folding a reusable absorbent insert, the method comprising:

folding a first section of a configurable pad over a second section of the configurable pad along a folding axis of a folding guide to form a semi-folded configuration, the folding guide at least partially separating the second section from the first section, the configurable pad having an unfolded pad plan surface area comprising an unfolded pad width when the reusable absorbent insert is in an unfolded, flat-out configuration, the semi-folded configuration comprising a semi-folded pad width, and the folding axis being transverse to the unfolded pad width and the semi-folded pad width; and folding a pad collection sleeve along an axis parallel to the semi-folded pad width into a folded, final configuration that at least partially covers the configurable pad, the pad collection sleeve having an unfolded sleeve plan surface area comprising an unfolded sleeve width when the reusable absorbent insert is in an unfolded, flat-out configuration, the unfolded pad width being greater than or substantially equal to the unfolded sleeve width and substantially equal to the semi-folded pad width.

* * * * *